(12) United States Patent
Bang et al.

(10) Patent No.: US 8,940,908 B2
(45) Date of Patent: Jan. 27, 2015

(54) METHOD FOR PREPARING TETRAZOLE METHANESULFONIC ACID SALTS, AND NOVEL COMPOUND USED IN SAME

(71) Applicant: Hanmi Science Co., Ltd, Hwaseong-si (KR)

(72) Inventors: Keuk Chan Bang, Incheon-si (KR); Bum Woo Park, Seoul (KR); Jong Won Choi, Seoul (KR); Jae Chul Lee, Suwon-si (KR); Yong Hoon An, Osan-si (KR); Young Gil Ahn, Seongnam-si (KR); Maeng Sup Kim, Seoul (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 0 days.

(21) Appl. No.: 14/171,318

(22) Filed: Feb. 3, 2014

(65) Prior Publication Data
US 2014/0148602 A1 May 29, 2014

Related U.S. Application Data

(62) Division of application No. 13/522,272, filed as application No. PCT/KR2011/000291 on Jan. 14, 2011, now Pat. No. 8,680,277.

(30) Foreign Application Priority Data

Jan. 15, 2010 (KR) .................. 10-2010-0003835

(51) Int. Cl.
C07D 417/12 (2006.01)
C07D 403/10 (2006.01)
C07D 405/12 (2006.01)
C07D 405/14 (2006.01)

(52) U.S. Cl.
CPC ............ *C07D 417/12* (2013.01); *C07D 403/10* (2013.01); *C07D 405/12* (2013.01); *C07D 405/14* (2013.01)
USPC ........................................ 548/159

(58) Field of Classification Search
None
See application file for complete search history.

(56) References Cited

U.S. PATENT DOCUMENTS

2005/0234054 A1 10/2005 Mueller et al.
2007/0161791 A1 7/2007 Penthala et al.

FOREIGN PATENT DOCUMENTS

WO 2005/033097 A1 4/2005

OTHER PUBLICATIONS

Sharma et al., "2,2'-Dibenzothiazolyl Disulfide: A Versatile Reagent for the Synthesis of 2-Azetidinones," Synlett, 2004, No. 15, pp. 2824-2826.
Singh et al., "2'-Benzothiazolylthioesters of N-Substituted Alpha Amino Acids: Versatile Intermediates for Synthesis of ACE Inhibitors," Synthetic Communications, 2005, vol. 35, No. 2, pp. 243-248.
European Patent Office, European Search Report issued in corresponding EP Application No. 11733103.3, dated Jun. 18, 2013.
International Searching Authority, International Search Report of PCT/KR2011/000291, dated Sep. 23, 2011.

*Primary Examiner* — Zinna Northington Davis
(74) *Attorney, Agent, or Firm* — Sughrue Mion, PLLC

(57) ABSTRACT

A method for preparing tetrazole methanesulfonic acid salts includes an acylation reaction using a novel 4-iodine-4H-chromene-2-carbothionic acid S-benzothiazole-2-yl ester. The method is advantageous that it can shorten a reaction time and improve safety as compared to conventional methods, and can prepare high-purity tetrazole methanesulfonic acid salts at a high yield rate without using a column chromatography method.

5 Claims, No Drawings

METHOD FOR PREPARING TETRAZOLE METHANESULFONIC ACID SALTS, AND NOVEL COMPOUND USED IN SAME

CROSS-REFERENCE TO RELATED APPLICATIONS

This application is a divisional of U.S. patent application Ser. No. 13/522,272 (allowed) filed on Aug. 21, 2012, which is a National Stage Application of PCT/KR2011/000291 filed on Jan. 14, 2011, which claims priority from Korean Patent Application No. 10-2010-0003835 filed on Jan. 15, 2010, the contents of which are hereby incorporated by reference in their entirety.

FIELD OF THE INVENTION

The present invention relates to a method for preparing tetrazole methanesulfonic acid salts and a novel compound used therein.

BACKGROUND OF THE INVENTION

Pharmaceutically acceptable salts of 4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxyphenyl]-amine, as P-glycoprotein inhibitor, are useful as a multidrug resistance inhibitor. PCT Publication No. WO 2005/033097 discloses a preparation method thereof.

According to the publication, as shown in Reaction Schemes 1 and 2, nitro-based compounds (1 and 3) undergo hydrogenation in a solvent such as methanol, ethanol, chloroform, dichloromethane, tetrahydrofuran, ethyl ether and hexane toluene, in the presence of a metal catalyst such as palladium, platinum and zinc to obtain amino compounds (2 and 4). The resulting compound is then subjected to an acylation using a condensing agent such as 1-(3-dimethylaminopropyl)-3-ethylcarbodiimide hydrochloride, N,N-dicyclohexyldiimide, N,N-diisoprocarbodiimide and 1-cyclohexyl-3-(2-morpholinoethyl)carbodiimide methyl-p-toluenesulfonate, in the presence of a catalyst such as 4-(dimethylamino)pyridine in a solvent such as dichloromethane, chloroform, N,N-dimethylformamide, tetrahydrofuran, and 1,4-dioxane, to obtain a tetrazole compound (5) as a final product.

Reaction Scheme 1

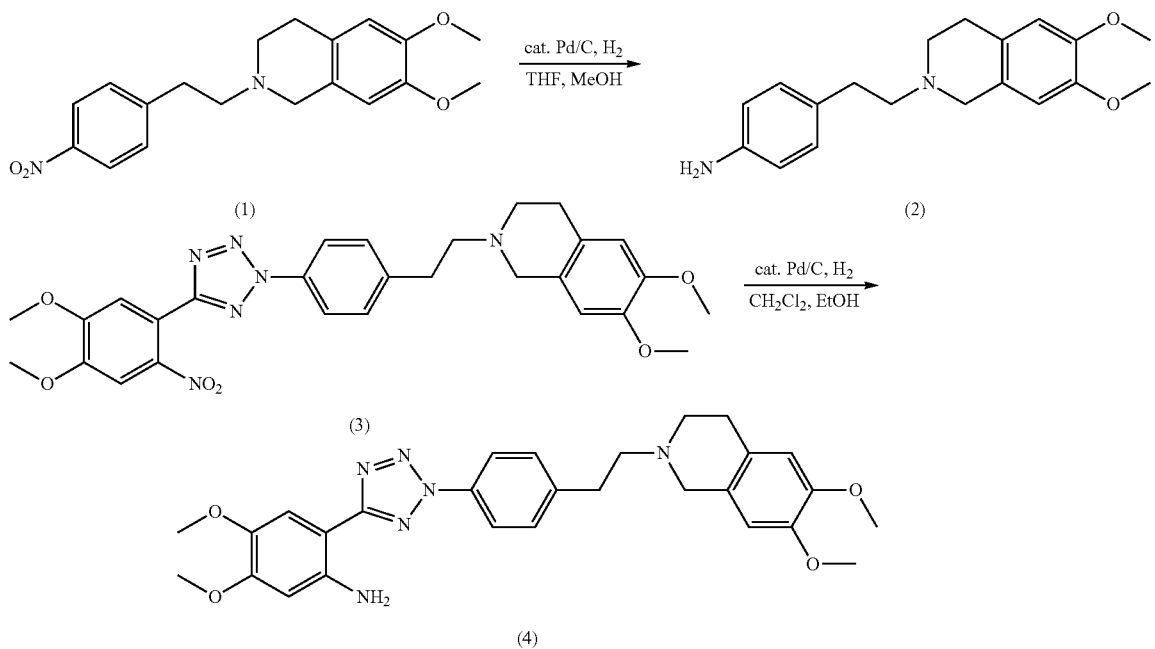

Reaction Scheme 2

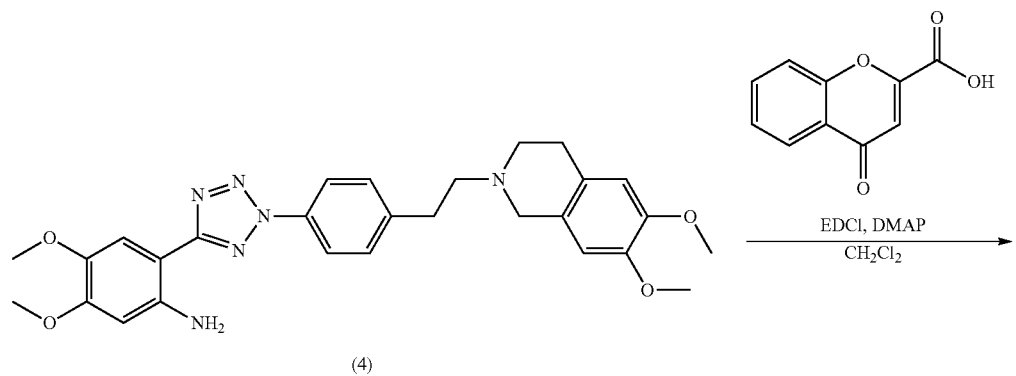

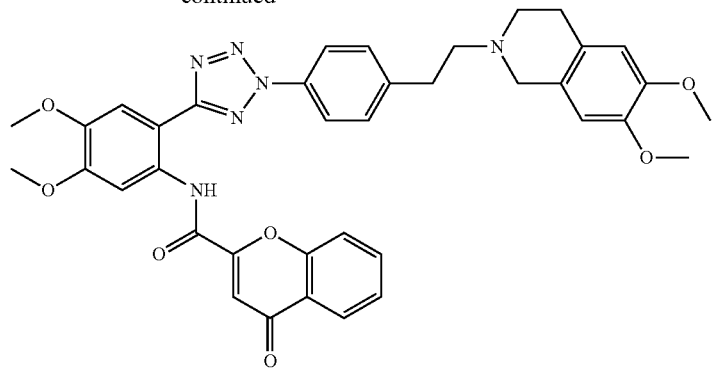

(5)

However, the conventional method may cause safety hazards such as explosion and fire owing to the employment of hydrogen and metal catalyst in large scale production. Also, it further needs a purification process using silica gel column chromatography in order to separate a pure tetrazole compound, which is impractical for large scale production since there are limitations on the size of the column and the amount of loading material in column chromatography. In addition, the chromatography process requires high operational costs due to high-priced column packing material, silica gel, and a large amount of eluent used for the process.

SUMMARY OF THE INVENTION

Accordingly, it is an object of the present invention to provide a novel method for preparing tetrazole methanesulfonic acid salts.

It is another object of the present invention to provide a novel compound which can be used for the preparation of the tetrazole methanesulfonic acid salt, and a method for preparing the same.

In accordance with one aspect of the present invention, there is provided a method for preparing the tetrazole methanesulfonic acid salt of formula (I), which comprises the steps of:

acylating the compound of formula (II) with the compound of formula (III) to obtain the compound of formula (IV); and adding methanesulfonic acid to the compound of formula (IV).

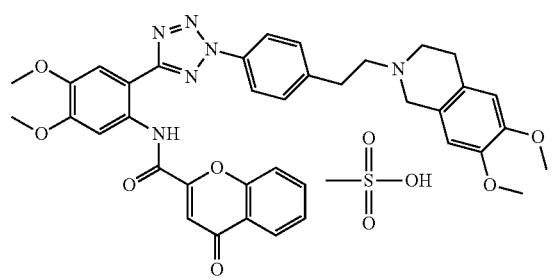

(I)

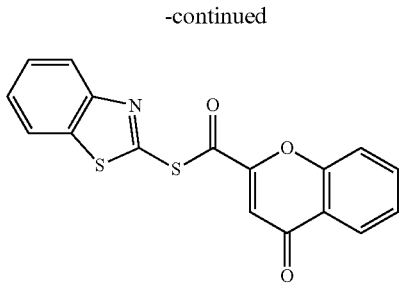

(II)

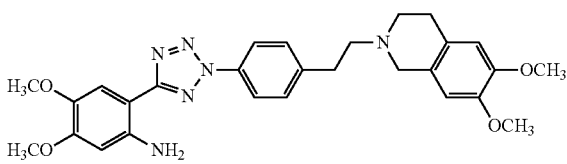

(III)

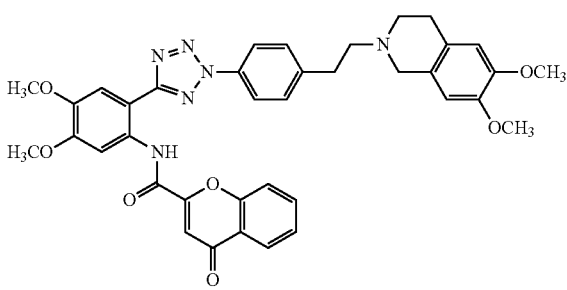

(IV)

In accordance with another aspect of the present invention, there is provided the compound of formula (II) which can be used for the preparation of the tetrazole methanesulfonic acid salt.

In accordance with a further aspect of the present invention, there is provided a method for preparing the compound of formula (II) comprising the step of reacting the compound of formula (V) with the compound of formula (VI) in the presence of triphenylphosphine and a base.

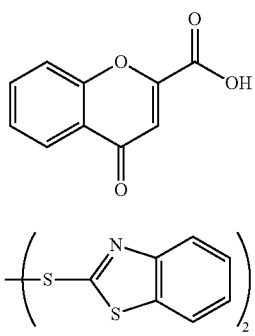

DETAILED DESCRIPTION OF THE INVENTION

Hereinafter, the present invention is described in detail.

The preparation method according to the present invention employs an acylation process using a novel compound, 4-oxo-4H-chromene-2-carbothionic acid S-benzothiazol-2-yl ester, instead of using a condensing agent as in conventional methods, to obtain tetrazole methanesulfonic acid salts with a high purity at a high yield, without an additional purification process such as a column chromatography.

As shown in Reaction Scheme 3 below, the method for preparing tetrazole methanesulfonic acid salts according to the present invention comprises: (Step 1) acylating the compound of formula (II) with the compound of formula (III) to obtain the compound of formula (IV); and (Step 2) adding methanesulfonic acid to the compound of formula (IV) obtained in the above step.

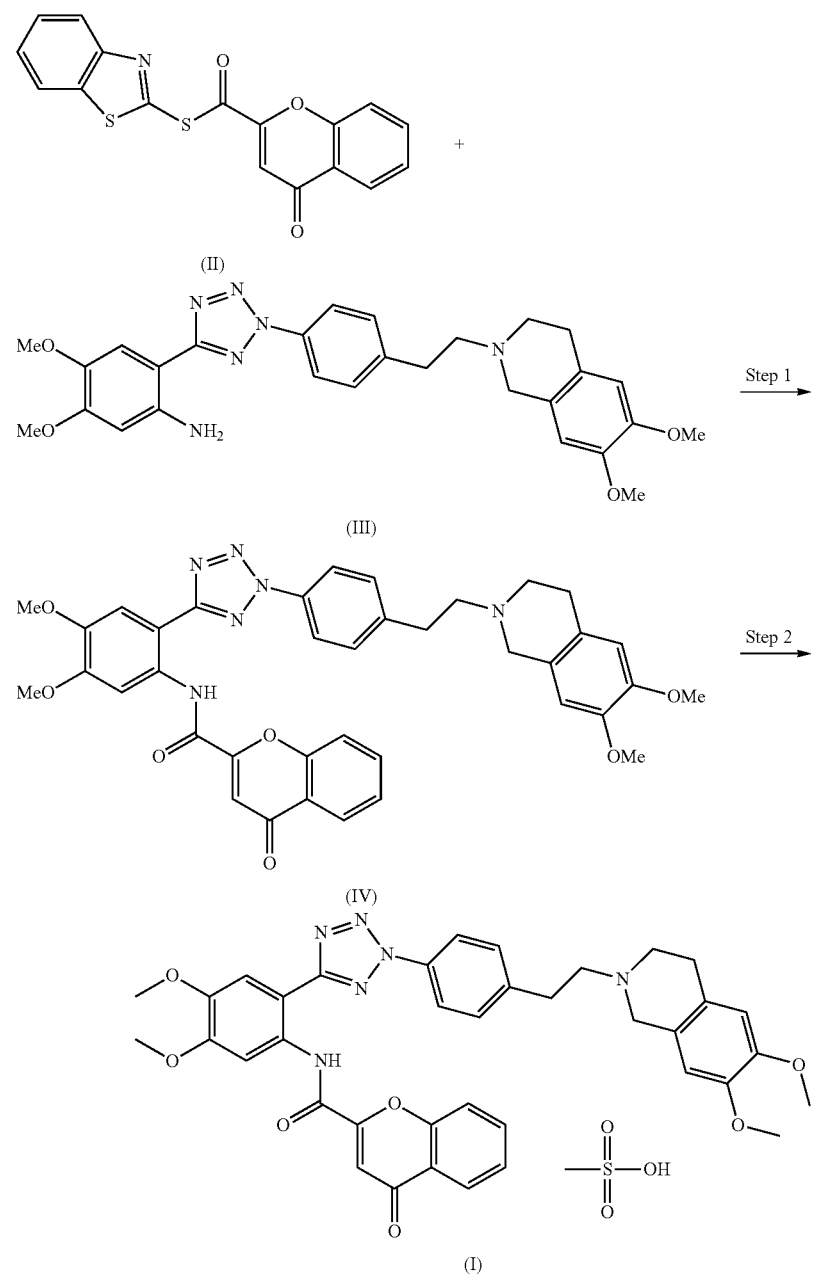

Reaction Scheme 3 wherein Me represents methyl group.

First, the compounds of formulas (II) and (III) undergo an acylation in a polar aprotic solvent to obtain the compound of formula (IV).

Specifically, the ester compound of formula (II) and the compound of formula (III) are subjected to an acylation in a polar aprotic solvent selected from the group consisting of dichloromethane, tetrahydrofuran, ethyl ester, acetone, N,N-dimethylformamide, acetonitrile, dimethyl sulfoxide and a mixture thereof, preferably dichloromethane. After the acylation is complete, methanol is added thereto in order to deactivate the remaining compound of formula (II). Subsequently, acetone is added thereto for purification so that the compound of formula (IV) with 98% or more purity can be yielded naturally and efficiently.

In the acylation, the compound of formula (II) is preferably employed in an amount of 1 to 5 equivalents based on 1 equivalent of the compound of formula (III).

In order to deactivate the remaining compound of formula (II) after the acylation, methanol is preferably employed at a volume to weight ratio (v/w) of 1 to 2, i.e., in a volume ranging from 1 to 2 mL based on 1 g of the compound of formula (II).

Also, acetone may be employed for purification in the acylation, wherein a preferable form of the acetone is an aqueous solution, more preferably 95% aqueous acetone. The acetone is preferably employed in a volume ranging from 35 to 45 mL based on 1 g of the compound of formula (III).

For the next step, methanesulfonic acid is added to the compound of formula (IV) obtained in the previous step to yield the tetrazole methanesulfonic acid salt of formula (I).

Specifically, the tetrazole compound of formula (IV) obtained in the previous step is dissolved in an organic solvent such as chloroform and methanol, followed by adding methanesulfonic acid thereto. Then ethyl acetate and acetone are added thereto, in sequence, for purification so that the tetrazole methanesulfonic acid salt of formula (I) can be yielded in a safe and effective way.

In the above process, methanesulfonic acid which acts as a conjugate acid of the compound of formula (IV) is preferably employed in an amount of 1 to 1.5 equivalents based on 1 equivalent of the compound of formula (IV).

Further, ethyl acetate and acetone may be used for purification. The ethyl acetate is preferably employed in a volume ranging from 1 to 5 mL based on 1 g of the compound of formula (IV). The acetone may be employed in an aqueous solution, preferably 95% aqueous acetone, in a volume ranging from 15 to 25 mL based on 1 g of the compound of formula (IV).

As stated in the above, the inventive method using the compound of formula (II) for preparing the tetrazole methanesulfonic acid salt may employ methanol and acetone only, without using a column chromatography, to obtain the compound of formula (IV) with a high purity at a high yield. Therefore, in comparison with conventional methods comprising an acylation using a condensing agent such as 1-(3-dimethylaminopropyl)-3-ethylcarbodiimide, N,N-dicyclohexyldiimide, N,N-diisoprocarbodiimide and 1-cyclohexyl-3-(2-(morpholinoethyl)carbodiimide methyl-p-toluensulfonate, the inventive method can prepare a high purity product through a simple filtration, and thus, it provides very cost-effective and convenient method suitable for large scale production.

Meanwhile, the compound of formula (II) employed in the above acylation (Step 1) may be prepared by reacting the compound of formula (V) with the compound of formula (VI) in the presence of triphenylphosphine and a base, as shown in Reaction Scheme 4 below.

Reaction Scheme 4

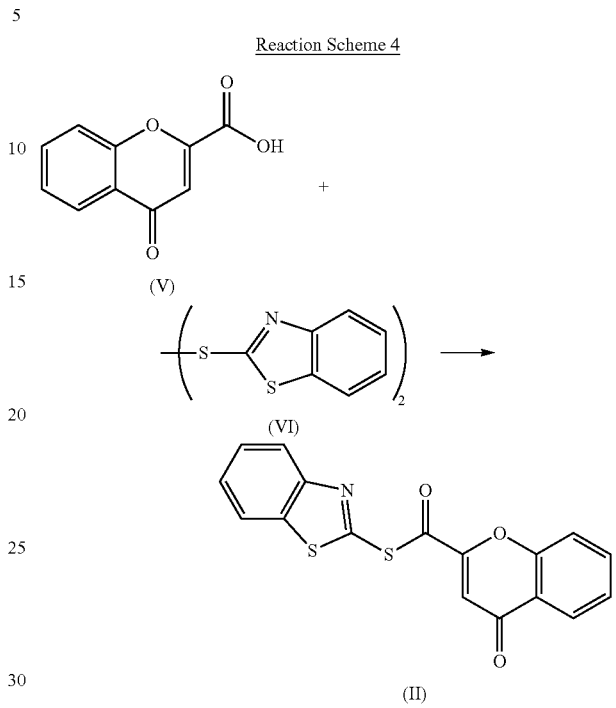

Specifically, 4-oxo-4H-chromene-2-carbothionic acid S-benzothiazol-2-yl ester of formula (II) may be prepared by reacting chromonic acid of formula (V) with 2,2'-dithiobis-benzothiazole of formula (VI) in an organic solvent in the presence of a base and triphenylphosphine (PPH₃) at a temperature ranging from 20 to 25° C. for 1 to 3 hours, wherein the organic solvent is selected from the group consisting of dichloromethane (CH₂Cl₂), diethyl ether, ethyl ester, tetrahydrofuran and a mixture thereof, preferably dichloromethane, and the base is selected from the group consisting of triethylamine (NEt₃), pyridine, imidazole, diisopropylethylamine (DIPEA), 4-dimethylaminopyridine (DMAP) and a mixture thereof, preferably triethylamine. If the reaction time exceeds 3 hours, there may form impurities as byproducts.

In the reaction, the amount of the compound of formula (VI) employed is preferably 1 to 2 equivalents based on 1 equivalent of the compound of formula (V).

Also, the triphenylphosphine is preferably employed in an amount of 1 to 2 equivalents based on 1 equivalent of the compound of formula (V).

The base is preferably employed in an amount of 1 to 2 equivalents based on 1 equivalent of chromonic acid of formula (V).

Further, the compound of formula (III) which is used as a starting material in the inventive method for preparing the tetrazole methanesulfonic acid salt may be prepared by the following method, as shown in Reaction Scheme 5, comprising: (Step 1) subjecting the compound of formula (VII) to a cyclization reaction with the compound of formula (VIII) to obtain the compound of formula (IX); and (Step 2) reducing the compound of formula (IX) obtained in the previous step by using a metal and an acid.

Reaction Scheme 5

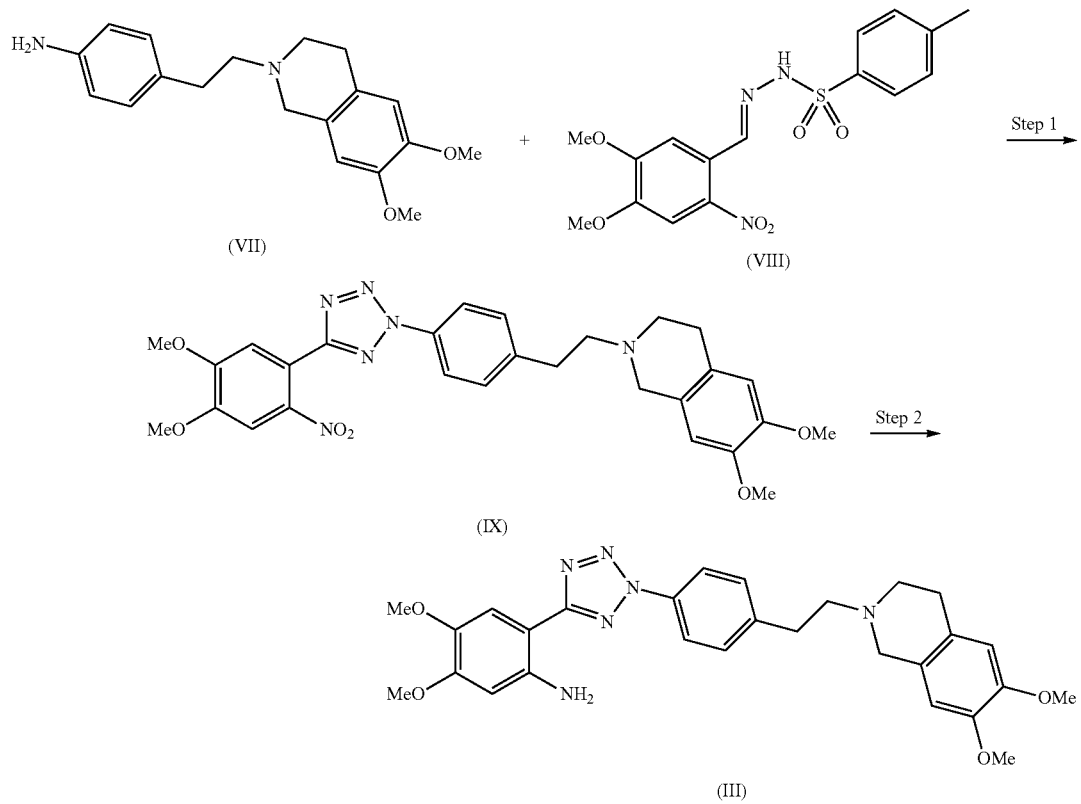

wherein Me represents methyl group.

First, the compounds of formulas (VII) and (VIII) undergo cyclization to obtain the nitrophenyl tetrazole compound of formula (IX).

Specifically, the compound of formula (VII) is allowed to react in the presence of sodium nitrite and hydrochloric acid in an aqueous solution, e.g., 50% ethanol solution, to obtain a diazonium salt. The compound of formula (VIII) and pyridine are added thereto and stirred while maintaining the reaction temperature at 10° C. or lower. The reaction mixture is heated to room temperature and further stirred, rinsed with 2.5 N hydrochloric acid solution, sodium bicarbonate and water, and then extracted with dichloromethane. After the organic layer is removed, methanol is added for crystallization to obtain the compound of formula (IX) as a final product [see Suketaka Ito et al., *Bulletin of the Chemical Society of Japan*, Vol 49(7), 1920-1923 (1976)].

Herein, the compound of formula (VII) may be prepared, as shown in Reaction Scheme 6 below, by reacting the compound of formula (X) with the compound of formula (XI) to obtain the compound of formula (XII), followed by reducing the compound of formula (XII) using a metal and an acid.

Reaction Scheme 6

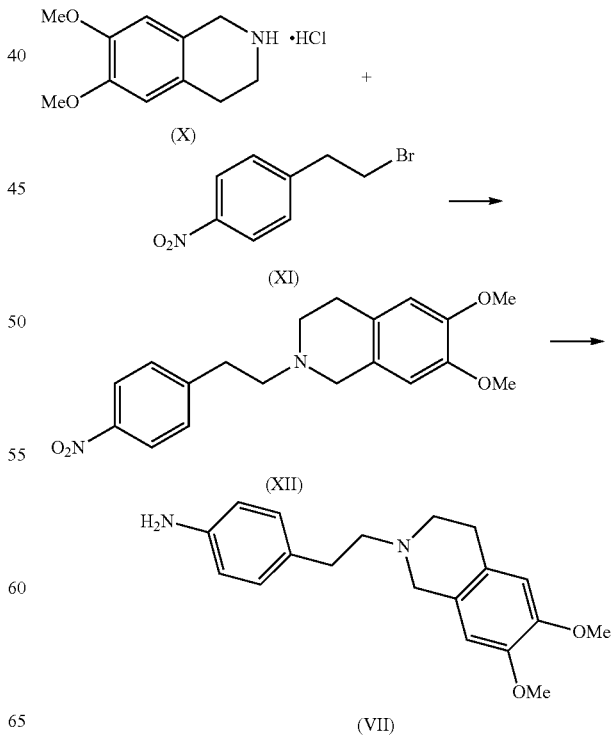

wherein Me represents methyl group.

Specifically, the compound of formula (X) is subjected to a reaction with the compound of formula (XI) in a solvent such as N,N-dimethylformaldehyde in the presence of anhydrous potassium bicarbonate ($K_2CO_3$) and sodium iodide (NaI) at a temperature ranging from 70 to 100° C. with stirring to obtain the nitrobenzene isoquinoline compound of formula (XII). Then the dried compound of formula (XII) is subjected to a reduction using a metal and an acid in an aqueous solution, e.g., 50% ethanol solution, to obtain the aminobenzene isoquinoline compound of formula (VII), wherein the metal is selected from the group consisting of iron, tin, zinc and nickel, preferably iron, and the acid is selected from the group consisting of hydrochloric acid, nitric acid, sulfuric acid, acetic acid and a mixture thereof.

The reduction may be conducted for 3 hours at 80° C. After the reduction, 10% aqueous solution of sodium chloride may be added thereto for neutralization, and filtered through a Celite pad. After the organic layer is removed, the residue is solidified with ethyl ether to obtain the compound of formula (VII). In the reduction, the metal may be employed in an amount of 2 to 10 equivalents based on 1 equivalent of the compound of formula (XII), and the acid may be employed in an amount of 0.1 to 0.5 equivalents based on 1 equivalent of the compound of formula (XII).

Further, the compound of formula (VIII) may be prepared, as shown in Reaction Scheme 7, by reacting the compound of formula (XIII) with the compound of formula (XIV).

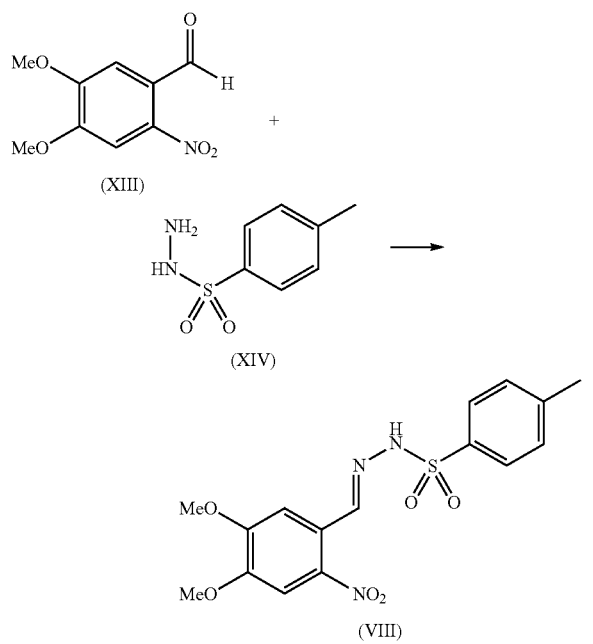

wherein Me represents methyl group.

Specifically, the compound of formula (XIII) is subjected to a reaction with the compound of formula (XIV) in ethanol at a temperature ranging from 70 to 80° C., followed by filtering and drying processes to obtain the compound of formula (VIII) [see Suketaka Ito et al., *Bulletin of the Chemical Society of Japan*, Vol 49(7), 1920-1923 (1976)].

In Reaction Scheme 5, the compound of formula (IX) obtained in Step 1 is then subjected to a reduction using a metal and an acid to prepare the compound of formula (III) (Step 2).

Specifically, the compound of formula (IX) is subjected to a reduction using a metal in an acid to obtain the compound of formula (III), wherein the metal is selected from the group consisting of iron, tin, zinc and nickel, preferably iron, and the acid is selected from the group consisting of hydrochloric acid, nitric acid, sulfuric acid, acetic acid and a mixture thereof, preferably acetic acid, e.g., 50% aqueous acetic acid.

The reduction is preferably conducted at 80° C. for 3 hours. After the reduction, the resulting mixture is filtered through a Celite pad, and then neutralized. After the organic solvent is removed, the residue is stirred in methanol to obtain the compound of formula (III).

In the reduction, the metal may be employed in an amount of 5 to 15 equivalents based on 1 equivalent of the compound of formula (IX), and the acid may be employed in a volume ranging from 2 to 5 mL based on 1 g of the compound of formula (IX).

The present invention, as stated in the above, employs a metal and an acid in reduction process during the production of the compounds of formulas (III) and (VII), instead of using palladium and gaseous hydrogen as in conventional methods, so that it can reduce the reaction time as well as risk of explosion due to an improved safety of the reduction.

According to another aspect of the present invention, there is provided the compound of formula (II) which is useful in preparation of the tetrazole methanesulfonic acid salt of formula (I):

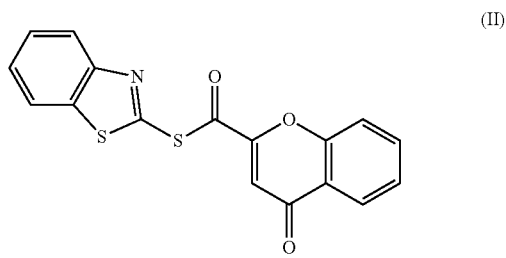 [SMILES: O=C(Sc1nc2ccccc2s1)c1cc(=O)c2ccccc2o1]

Further, there is provided a method for preparing the compound of formula (II) comprising the step of reacting the compound of formula (V) with the compound of formula (VI) in the presence of a base:

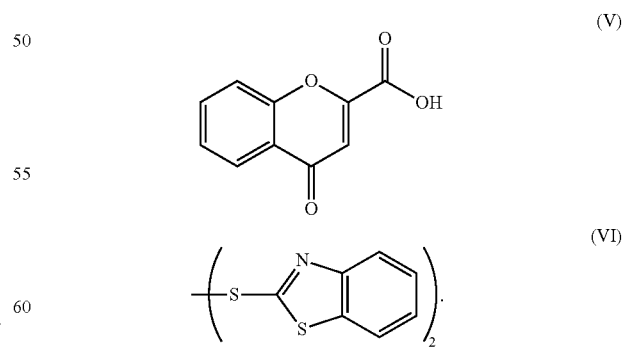

Hereinafter, the present invention is described more specifically by the following examples, but these are provided only for illustration purposes, and the present invention is not limited thereto.

EXAMPLE

Preparation of N-(2-(2-(4-(2-(6,7-dimethoxy-3,4-dihydroisoquinoline-2(1H)-yl)ethyl)phenyl)-2H-tetrazol-5-yl)-4,5-dimethoxyphenyl)-4-oxo-4H-chromene-2-carboxamide methanesulfonic acid salt

Step 1-1) 6,7-dimethoxy-2-(4-nitrophenethyl)-1,2,3,4-tetrahydroisoquinoline

5 L of N,N-dimethylformamide, 2-(4-nitrophenyl)ethyl bromide (1.0 kg, 4.35 mol) and 6,7-dimethoxy-1,2,3,4-tetrahydro-isoquinoline hydrochloride (DTIH; 1.0 kg, 4.35 mol) was added to a reactor, and stirred. Potassium carbonate (1.80 kg, 13 mol) and sodium iodide (780 g, 5.20 mol) were added thereto, the reactor was heated to 100° C., and further stirred for 12 hours. After checking completion of the reaction by thin layer chromatography (eluent: chloroform/methanol=15/1), the reaction mixture was cooled to room temperature.

20 L of cool water was added to a separate reactor and then the reaction mixture obtained in the previous step was slowly added thereto, followed by stirring for 4 hours. The resulting mixture was filtered, washed with 3 L of water, and then dried with hot air at 40° C. in an oven to obtain the title compound (1.34 kg, 90%).

$^1$H-NMR(CDCl$_3$) d: 8.17(d, 2H), 7.43(d, 2H), 6.62(s, 1H), 6.54(s, 1H), 3.87(s, 3H), 3.85(s, 3H), 3.66(s, 2H), 3.03(t, 2H), 2.82-2.78(m, 6H)

Step 1-2) 4-(2-(6,7-dimethoxy-3,4-dihydroisoquinoline-2(1H)-yl)-ethyl)-benzenamine Iron (1.27 kg, 23.48 mol), hydrochloric acid (127 mL, 1.54 mol) and 6.7 L of 50% aqueous ethanol were added to a reactor, and stirred for 1 hour at 80° C. 6,7-dimethoxy-2-(4-nitrophenethyl)-1,2,3,4-tetrahydroisoquinoline (1.3 kg, 3.91 mol) obtained in Step 1-1 was slowly added thereto for one hour, followed by stirring for 3 hours at 80° C. After checking completion of the reaction by thin layer chromatography (eluent: chloroform/methanol=15/1), the reaction mixture was cooled to room temperature. 5.3 L of dichloromethane and 5.3 L of water were added thereto, the reaction mixture was neutralized by adding 804 mL of 10% aqueous sodium hydroxide. The resulting mixture was filtered through a Celite pad and washed with 3 L of methylenechloride. The organic layer was collected, dried over magnesium sulfate, and then filtered. The solvent was removed under reduced pressure, and dried with hot air at 40° C. in an oven to obtain the title compound (1.05 kg, 90%).

$^1$H-NMR(CDCl$_3$) d: 7.02(d, 2H), 6.65-6.53(m, 4H), 3.84 (s, 3H), 3.83(s, 3H), 3.63(s, 2H), 3.57(s, 2H), 2.84-2.86(m, 8H).

Step 2) 4,5-dimethoxy-2-nitro-p-toluenesulfonylhydrazone 12.5 L of ethanol, p-toluenesulfonylhydrazide (1 kg, 5.37 mol) and 6-nitroveratraldehyde (1.2 kg, 5.907 mol) were added to a reactor, and then heated to 80° C., followed by stirring for 6 hours. After checking completion of the reaction by thin layer chromatography (eluent: chloroform/methanol=15/1), the reaction mixture was cooled to room temperature. The resulting mixture was filtered, washed with 12.5 L of ethanol, and then dried with hot air at 40° C. in an oven to obtain the title compound (1.47 kg, 99.6%).

$^1$H-NMR(CDCl$_3$) d: 8.48(s, 1H), 8.08(s, 1H), 7.89(d, 2H), 7.59(s, 1H), 7.42(s, 1H), 7.33(d, 2H), 4.02(s, 3H), 3.98(s, 3H), 2.44(s, 3H).

Step 3) 4-oxo-4H-chromene-2-carbothionic acid S-benzothiazol-2-yl ester

Chromone-2-carboxylic acid (700 g, 3.68 mol), 2,2'-dithiobis-benzothiazol (1.47 kg, 4.42 mol), triphenylphosphine (1.16 kg, 4.42 mol) and 14.7 L of dichloromethane were added to a reactor, and stirred. Triethylamine (616 mL, 4.42 mol) in 2 L of dichloromethane was slowly added to the reaction mixture, and stirred for 6 hours. After completion of the reaction, the resulting mixture was filtered, washed with 4 L of acetone, and then dried with hot air at 40° C. in an oven to obtain the title compound (0.99 kg, 80%).

$^1$H-NMR(CDCl$_3$) d: 8.30(d, 1H), 8.16(d, 1H), 8.01(d, 1H), 7.88(t, 1H), 7.70(d, 1H), 7.61-7.31(m, 3H), 7.15(s, 1H)

Step 4) 2-(4-(5-(4,5-dimethoxy-2-nitrophenyl)-2H-tetrazol-2-yl)phenethyl)-6,7-dimethoxy-1,2,3,4-tetrahydroisoquinoline 4-(2-(6,7-dimethoxy-3,4-dihydroisoquinoline-2(1H)-yl)-ethyl)-benzenamine (1.0 kg, 3.2 mol) obtained in Step 1-2, 3 L of 50% aqueous ethanol, and hydrochloric acid (850 mL, 12.5 mol) were added to a reactor A, and stirred at 0° C. Sodium nitrite (227 g, 3.3 mol) in 330 mL of water was slowly added to the reaction mixture, and stirred for 3 hours.

4,5-dimethoxy-2-nitro-p-toluenesulfonyl-hydrozone (1.2 kg, 3.2 mol) obtained in Step 2 and 12 L of pyridine were added to a 20 L reactor B, and cooled to 0° C. The mixture from the reactor A was slowly added thereto, followed by stirring for 6 hours at room temperature. After checking completion of the reaction by thin layer chromatography (eluent: chloroform/methanol=15/1), the reaction mixture was subject to an extraction with 12 L of dichloromethane and 12 L of water. The organic layer was collected, washed three times with 18 L of 2.5 N hydrochloric acid and washed with a sodium bicarbonate solution. The organic layer was dried, and distilled under reduced pressure. The residue was mixed with 10 L of methanol, and stirred for 4 hours. The resulting mixture was filtered and dried with hot air at 40° C. in an oven to obtain the title compound (1.08 kg, 62%).

$^1$H-NMR(CDCl$_3$) d: 8.08(d, 2H), 7.66(s, 1H), 7.45(d, 2H), 7.32(s, 1H), 6.59(d, 2H), 4.03(s, 6H), 3.85(s, 6H), 3.68(s, 2H), 3.01(m, 2H), 2.84(m, 6H).

Step 5) 2-(2-(4-(2-(6,7-dimethoxy-3,4-dihydroisoquinoline-2(1H)-yl)ethyl)phenyl)-2H-tetrazol-5-yl)-4,5-dimethoxybenzenamine Iron (433 g, 7.76 mol) and 5.4 L of 50% aqueous acetic acid were added to a reactor, and stirred for 1 hour at 80° C. 2-(4-(5-(4,5-dimethoxy-2-nitrophenyl)-2H-tetrazol-2-yl)phenethyl)-6,7-dimethoxy-1,2,3,4-tetrahydroisoquinoline (1.06 kg, 1.94 mol) obtained in Step 4 was slowly added thereto for two hours, followed by stirring for 1 hour. After checking completion of the reaction by thin layer chromatography (eluent: chloroform/methanol=15/1), the reactor was cooled to room temperature. 5.3 L of chloroform and 2.4 L of water were added thereto and the resulting mixture was filtered through a Celite pad. The organic layer was collected, 6.6 L of saturated sodium bicarbonate solution was slowly added thereto with stirring. The organic layer was collected, and the aqueous layer was further extracted using 1.25 L of chloroform. The resulting organic layer was dried over magnesium sulfate, and then distilled under reduced pressure to remove the solvent. The residue was mixed with 10.6 L of methanol, followed by stirring. The resulting mixture was filtered, and dried with hot air at 40° C. in an oven to obtain the title compound (0.87 kg, 87%).

$^1$H-NMR(CDCl$_3$) d: 8.14(d, 2H), 7.75(s, 1H), 7.49 (d, 2H), 6.63 (d, 2H), 6.40 (s, 1H), 5.34(d, 2H), 3.97(d, 6H), 3.89(s, 6H), 3.72(s, 2H), 3.06(t, 2H), 2.91-2.84(m, 6H)

Step 6) N-(2-(2-(4-(2-(6,7-dimethoxy-3,4-dihydroisoquinoline-2(1H)-yl)ethyl)phenyl)-2H-tetrazol-5-yl)-4,5-dimethoxyphenyl)-4-oxo-4H-chromene-2-carboxamide 2-(2-(4-(2-(6,7-dimethoxy-3,4-dihydroisoquinoline-2(1H)-yl)ethyl)phenyl)-2H-tetrazol-5-yl)-4,5-dimethoxybenzenamine (850 g, 1.6 mol) obtained in Step 5, 4-oxo-4H-chromene-2-carbothionic acid S-benzothiazol-2-yl ester (723 g, 2.1 mol) obtained in Step 3, and 17 L of dichloromethane were added to a reactor, and stirred for 6 hours at room temperature. After checking completion of the reaction by thin layer chromatography (eluent: chloroform/methanol=15/1), 1.1 L of methanol and 35.7 L of 95% aqueous acetone were added thereto, in sequence, followed by stirring for 16 hours at room temperature. The resulting mixture was filtered, washed with 4.3 L of acetone, dried with hot air at 40° C. in an oven to obtain the title compound (1.10 kg, 97%).

$^1$H-NMR(CDCl$_3$) d: 12.53(s, 1H), 8.60(s, 1H), 8.23(d, 1H), 8.14(d, 2H), 7.77(d, 2H), 7.74(s, 1H), 7.50-7.44(m, 3H), 7.26(d, 2H), 6.60(d, 2H), 4.01(s, 6H), 3.87(s, 6H), 3.70(s, 2H), 3.08(t, 2H), 3.02-2.83(m, 6H)

Step 7) N-(2-(2-(4-(2-(6,7-dimethoxy-3,4-dihydroisoquinoline-2(1H)-yl)ethyl)phenyl)-2H-tetrazol-5-yl)-4,5-dimethoxyphenyl)-4-oxo-4H-chromene-2-carboxamide methanesulfonic acid salt N-(2-(2-(4-(2-(6,7-dimethoxy-3,4-dihydroisoquinoline-2(1H)-yl)ethyl)phenyl)-2H-tetrazol-5-yl)-4,5-dimethoxyphenyl)-4-oxo-4H-chromene-2-carboxamide (1.06 kg, 1.54 mol) obtained in Step 6 was dissolved in a mixed solution of 18.1 L of chloroform and 1.06 L of methanol, and the resulting mixture was filtered. Methanesulfonic acid (102 mL, 1.57 mol) in 300 mL of ethyl acetate was slowly added thereto for 30 minutes. 3.95 L of ethyl acetate was slowly added thereto for 1 hour, followed by stirring for 16 hours at room temperature. The resulting mixture was filtered, washed with 1 L of ethyl acetate, and dried with hot air at 40° C. in an oven.

The product was subjected to a first recrystallization using chloroform, and then filtered, washed with ethyl acetate, and dried with hot air at 40° C. in an oven.

The dried solid was subjected to a second recrystallization using a mixed solvent (dichloromethane/methanol/ethyl acetate=17/1/4) to obtain a crystalline solid. To remove the residual solvent, i.e., dichloromethane, the product was mixed with 95% aqueous acetone, followed by stirring for 16 hours. The resulting mixture was filtered, and dried with hot air at 40° C. in an oven to obtain the title compound (0.84 kg, 70%).

Mass (ESI) calcd for C$_{38}$H$_{36}$N$_6$O$_7$; m/z 688.26 (M+H)+; found, m/z 689.32 (M+H)+

$^1$H-NMR(CDCl$_3$) d: 12.43(s, 1H), 11.66(s, 1H), 8.49(s, 1H), 8.17(d, 1H), 8.06(d, 2H), 7.79-7.67(m, 2H), 7.54(d, 3H), 7.46(t, 1H), 7.14(s, 1H), 6.67(d, 2H), 4.78(d, 1H), 4.19-4.12 (m, 1H), 3.96-3.87(m, 12H), 3.56-3.36(m, 6H), 3.04(d, 1H), 2.78(s, 3H).

Comparative Example

A tetrazole methanesulfonic acid was prepared in accordance with the procedures disclosed in WO 2005/033097, which comprise a reduction using palladium and gaseous hydrogen, and an acylation using 1-ethyl-3-(3-dimethylaminopropyl)carbodiimide hydrochloride (EDCI) and a condensing agent of 4-dimethylaminopyridine (DMAP).

Experimental Example

In order to compare the inventive method comprising a reduction using a metal and an acid to a conventional method using palladium and hydrogen, the purity of product, safety and economic feasibility of reduction processes in Example and Comparative Example were evaluated, and the results are summarized in Table 1, wherein the result of Comparative Example was referenced to 2009-2010 Aldrich Catalog.

As shown in Table 1, both reduction processes yielded target products with the same purity, however, the reduction process according to the present invention was able to prepare the target product in more safe, no explosion risks, and cost effective way in comparison to the conventional method.

TABLE 1

|  | Example | Comparative Example |
|---|---|---|
| Reducing agent | Iron/Acid | Palladium/Hydrogen |
| Purity of product | 95% | 95% |
| Safety | Good | Explosive (solvent vapors, gaseous H$_2$) |
| Economic feasibility of reducing agent | Inexpensive (1 g: 123 KRW) used in an amount of 40% of the weight of the reactant for preparation of the compound of formula (III) used in an amount of 40% of the weight of the reactant for preparation of the compound of formula (VII) | Expensive (1 g: 37,000 KRW) used in an amount of 10% of the weight of the reactant |

Also, in order to compare the efficiency of the inventive method using the compound of formula (II) to the conventional method using 1-ethyl-3-(3-dimethylaminopropyl)carbodiimide hydrochloride (EDCI) and 4-dimethylaminopyridine (DMAP) as condensing agent, the percent yield, purity and purification method of the compounds of formula (IV) in Example and Comparative Example are summarized in Table 2 below.

As shown in Table 2, the inventive method can produce the compound of formula (IV) with a higher percent yield and purity in comparison to the conventional method. It also can be shown that the inventive method can obtain a pure chemical product through recrystallization only, without an additional column chromatography process.

TABLE 2

|  | Example | Comparative Example |
|---|---|---|
| Compound used | Compound of formula (II) | EDCI/DMAP |
| Yield | 95% | 65% |
| Purity | >98% | 94% |
| Purification method | Recrystallization | Column chromatography |

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (II):

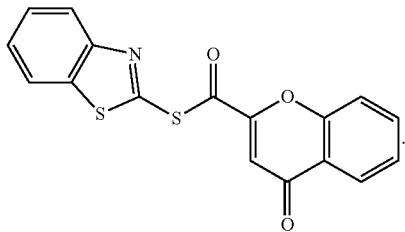 (II)

2. A method of preparing the compound of formula (II), which comprises the step of reacting the compound of formula (V) with the compound of formula (VI) in the presence of triphenylphosphine and a base:

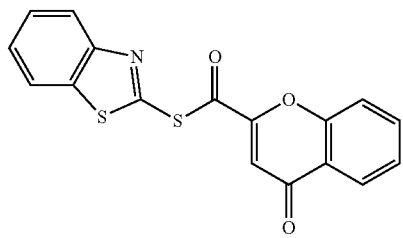 (II)

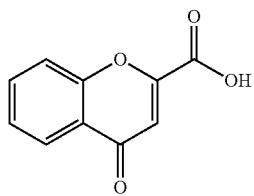 (V)

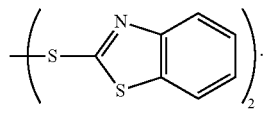 (VI)

3. The method of claim 2, wherein the base is selected from the group consisting of triethylamine, pyridine, imidazole, diisopropylethylamine and 4-dimethylamino pyridine.

4. The method of claim 2, wherein the reaction is conducted in an organic solvent selected from the group consisting of dichloromethane, diethyl ether, ethyl ester, tetrahydrofuran and a mixture thereof.

5. The method of claim 2, wherein the reaction is conducted with stirring for 1 to 3 hours at a temperature ranging from 20 to 25° C.

* * * * *